United States Patent [19]

Kvita et al.

[11] Patent Number: 4,506,083
[45] Date of Patent: Mar. 19, 1985

[54] THIOXANTHONECARBOXYLIC ACID ESTERS, THIOESTERS AND AMIDES

[75] Inventors: Vratislav Kvita, Muttenz; Hans Zweifel, Basel; Martin Roth, Marly; Louis Felder, Basel, all of Switzerland

[73] Assignee: Ciba-Geigy Corporation, Ardsley, N.Y.

[21] Appl. No.: 392,922

[22] Filed: Jun. 28, 1982

Related U.S. Application Data

[63] Continuation of Ser. No. 150,391, May 16, 1980, abandoned.

[30] Foreign Application Priority Data

May 18, 1979 [CH] Switzerland ............... 4671/79

[51] Int. Cl.³ .................................. C07D 335/16
[52] U.S. Cl. ..................... 549/27; 544/145; 546/202; 548/525; 260/465 D; 260/455 R; 560/11; 560/12; 560/13; 560/14; 560/17
[58] Field of Search .......................... 549/27

[56] References Cited

U.S. PATENT DOCUMENTS

| | | | |
|---|---|---|---|
| 3,642,997 | 2/1972 | Shen et al. | 549/27 X |
| 3,759,807 | 9/1973 | Osborn et al. | 549/27 X |
| 3,904,647 | 9/1975 | Pfister et al. | 549/27 |
| 3,981,887 | 9/1976 | Gante et al. | 549/27 X |
| 4,103,015 | 7/1978 | Hodson et al. | 424/269 |
| 4,185,108 | 1/1980 | Samour et al. | 424/274 |
| 4,348,530 | 9/1982 | Kvita et al. | 549/27 |
| 4,385,182 | 5/1983 | Fischer et al. | 549/27 |

FOREIGN PATENT DOCUMENTS 2325300 12/1973 Fed. Rep. of Germany .
2344799 3/1974 Fed. Rep. of Germany .
1447032 8/1976 United Kingdom .

OTHER PUBLICATIONS

1972–1976 Chem. Substance Index, (of Chemical Abstracts) p. 38465cs.

*Primary Examiner*—Joseph Paul Brust
*Attorney, Agent, or Firm*—Harry Falber

[57] ABSTRACT

Thioxanthonecarboxylic acid esters, thioesters or amides of the formula I

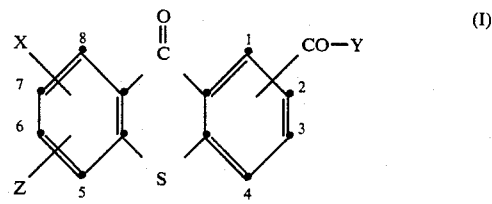

in which X and Z are hydrogen or one of the substituents defined in more detail in claim 1 and Y is $-OR_1$, $-SR_1$ or $-N(R_1)(R_2)$, in which $R_1$ is $C_{1-24}$alkyl and $R_2$ is H or $R_1$, are suitable, if desired together with amines, as initiators for the photopolymerization of ethylenically unsaturated compounds or for photochemical crosslinking of polyolefines. They are also used an sensitizers for photocrosslinkable polymers. They can be prepared by methods known per se, for example by cyclization of phenylthio-phthalic, -isophthalic or -terephthalic acids, which can be correspondingly substituted, and subsequent reaction with suitable alcohols, thiols or amines.

5 Claims, No Drawings

THIOXANTHONECARBOXYLIC ACID ESTERS, THIOESTERS AND AMIDES

This is a continuation of application Ser. No. 150,391 filed on May 16, 1980, now abandoned.

The present invention relates to novel Thioxanthonecarboxylic acid esters, thioesters and amides, processes for their preparation and their use as sensitisers for photocrosslinkable polymers or as initiators, if desired as a mixture with aminos, for the photopolymerisation of ethylenically unsaturated compounds or for photochemical crosslinking of polyolefines.

It is known that thioxanthone is suitable as a sensitiser for photo-induced crosslinking reactions. The prerequisite for a successful application of this type is good compatibility of the sensitiser in the polymer, i.e. the sensitiser must be miscible in up to fairly high concentrations with the polymer. Furthermore, the sensitisers must be readily soluble in the solvents used when processing the polymers. Unsubstituted thioxanthone, which is a known compound, does not satisfy these requirements in all respects; in particular, it easily separates in the polymer, as a result of which its sensitiser effect is severely impaired.

Novel thioxanthone derivatives have now been found which are outstandingly suitable for use as sensitisers for photocrosslinkable polymers, in that they meet in full the abovementioned requirements with respect to compatibility with the polymer and solubility in conventional organic solvents. Moreover, suprisingly, UV absorption can be so influenced by the novel thioxanthone derivatives according to the invention that these exert a sensitising action even on irradiation with long-wave UV light (up to 450 nm) and thus effect crosslinking of the photosensitive polymers.

It is also known that the photopolymerisation of ethylenically unsaturated compounds can be initiated by aromatic ketones of the benzophenone, anthraquinone, xanthone and thioxanthone type. Furthermore, it has been disclosed in U.S. Pat. No. 3,759,807 that the initiator effect of such aromatic ketones can be accelerated by the addition of organic amines. Since these amines on their own usually possess no initiator effect, they act in combination with aromatic ketones as activators or accelerators. Industrially this is of great importance, since the speed at which photochemically cured coatings or printing inks are produced depends in particular on the rate at which the unsaturated compound is polymerised.

Compared with the known mixtures mentioned above, mixtures of thioxanthone derivatives according to the invention with organic amines as initiators for the photopolymerisation of ethylenically unsaturated compounds, or for photochemical crosslinking of polyolefines, are distinguished by a higher polymerisation rate, by a lower tendency to yellowing in the case of coatings containing white pigment, by better solubility in the substrate and/or by increased stability on storage.

The thioxanthonecarboxylic acid esters, thioesters and amides according to the invention have the formula I

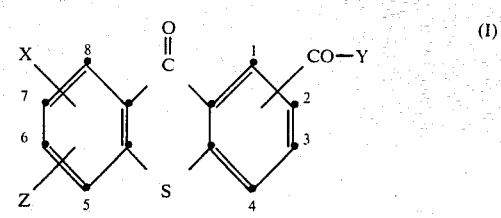

in which X is hydrogen, halogen, —CN, —OH, —SH, —NH$_2$, —NO$_2$, —SO$_3$H, phenylsulfonyl or alkylsulfonyl, alkyl, alkoxy, alkylthio, alkylamino, dialkylamino or —CO—alkyl, each having 1-4 C atoms in the alkyl moieties, —CO—OR$_1$, —CO—SR$_1$, —CO—N(R$_1$)(R$_2$), —CO—piperidyl, —CO—pyrrolidinyl or —CO—morpholinyl, Z is hydrogen, halogen, —OH, —SH or alkyl, alkoxy, alkylthio or dialkylamino having 1-4 C atoms in the alkyl moieties, Y is —OR$_1$, —SR$_1$, —N(R$_1$)(R$_2$), piperidyl, pyrrolidinly or morpholinyl, R$_1$ is alkyl having 1-24 C atoms, alkoxyalkyl having 3-10 C atoms, C$_5$-C$_8$—cycloalkyl, phenyl, naphthyl, —(CH$_2$)$_m$—phenyl or —(CH$_2$CH$_2$O)$_n$—CH$_3$, R$_2$ is hydrogen or a R$_1$ radical, m is the number 1 or 2 and n is an integer from 2 to 10, at least one of X and Z differing from hydrogen if the grouping —CO—Y is in the 4-position and Y is —OCH$_3$.

Alkyl, alkoxy and alkylthio groups X, Z, R$_1$ and R$_2$ and alkyl moieties in the radicals X or Z can be straight-chain or branched.

Examples or alkyl, alkoxy, alkoxyalkyl, alkylthio, alkylsulfonyl, N-alkylamino, N,N-dialkylamino and —CO—alkyl groups X, Z, R$_1$ or R$_2$ according to the definition are: the methyl, ethyl, n-propyl, isopropyl, n-butyl, sec.-butyl, n-pentyl, 2- or 3-pentyl, n-hexyl, n-heptyl, 2- or 3-heptyl, n-octyl, n-nonyl, n-decyl, 2-decyl, n-dodecyl, n-tetradecyl, n-hexadecyl, n-octadecyl, tridec-7-yl, heptadec-9-yl, 2,6,10-trimethyldodecyl and 2,6,10,14-tetramethylhexadecyl groups; the methoxy, ethoxy, n-propoxy, isopropoxy and n-butoxy group; the 2-methoxyethyl, 2-isopropoxyethyl, 2-butoxyethyl or 3-methoxypropyl group; the methylthio, ethylthio and n-propylthio group; the methylsulfonyl and ethylsulfonyl group; the methylamino, ethylamino, n-propylamino and n-butylamino group; the dimethylamino, diethylamino, methylethylamino and di-n-propylamino group and the acetyl, propionyl and butyryl group.

R$_1$ and R$_2$ in a CO—OR$_1$, —CO—SR$_1$ or —CO—N(R$_1$)(R$_2$) group X preferably have the same meaning as in the radicals Y.

R$_1$ is preferably alkyl having a total of 1 to 18 and in particular 1-12 C atoms, cyclohexyl or alkoxyalkyl having 3-8 C atoms.

Preferred compounds of the formula I are those in which X is hydrogen, or X and Z are hydrogen, and the group —CO—Y is bonded in the 1-position or 3-position.

A further category of preferred compounds of the formula I comprises those in which Y is —OR$_1$ or —N(R$_1$)(R$_2$) and especially those in which Y is —OR$_1$ and R$_1$ is alkyl having 1-18 C atoms, cyclohexyl or alkoxyalkyl having 3-8 C atoms.

Further preferred compounds of the formula I are those in which Z is bonded in the 7-position and is chlorine, alkyl, alkoxy or alkylthio.

Particularly preferred compounds of the formula I are those in which X is hydrogen, Z is hydrogen, chlorine, alkyl or alkoxy, the group —CO—Y is bonded in the 1-position or 3-position and Y is alkoxy having 1–18 C atoms, alkoxyalkyl having 3–6 C atoms or alkylamino or dialkylamino having 1–4 C atoms in the alkyl moiety.

The compounds of the formula I can be prepared, for example, by cyclising a compound of the formula IIa or IIb

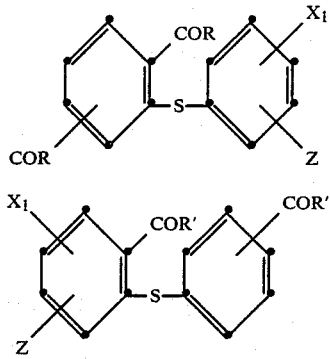

in which Z is as defined under formula I, $X_1$ is hydrogen, halogen, —CN, —OH, —SH, —NO$_2$, —SO$_3$H, —COOH, phenylsulfonyl or alkylsulfonyl, alkyl, alkoxy, alkylthio, N,N-dialkylamino or —CO—alkyl, each having 1–4 C atoms in the alkyl moieties, —CO—OR$_1$ or —CO—SR$_1$ and R$_1$ is as defined under forumla I, and R and R' are —OH, or, if the two —COR groups are in the ortho-position relative to one another, the two Rs together are —O—, to give a compound of the formula III

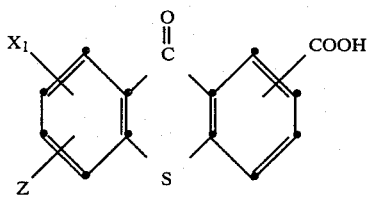

reacting the compound of the formula III, if desired after prior conversion to the corresponding acid chloride, with a compound HY and, if desired, subsequently converting the group $X_1$ to a group X which differs from $X_1$.

Preferably, the starting material used is a compound of the formula IIa in which the two —COR groups are in the ortho-position or para-position, and by this means intermediates of the formula III are obtained in which the carboxyl group is in the 1-position or 3-position.

According to a further process, compounds of the formula Ia

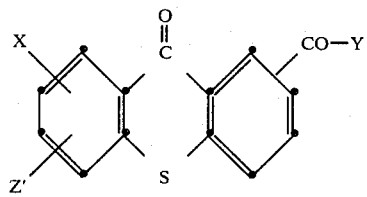

in which Z' is hydrogen, halogen or alkyl, alkoxy, alkylthio or dialkylamino, each having 1–4 C atoms in the alkyl moieties, can also be obtained by either (a) cyclising a compound of the formula Va

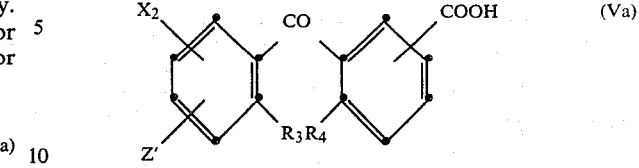

in which $X_2$ is hydrogen, halogen, —CN, NO$_2$, —SO$_3$H, —COOH, phenylsulfonyl or alkylsulfonyl, alkyl, alkoxy, alkylthio or dialkylamino, each having 1–4 C atoms in the alkyl moieties, and one of $R_3$ and $R_4$ is a mercapto group and the other is a detachable group, to give a compound of the formula VI

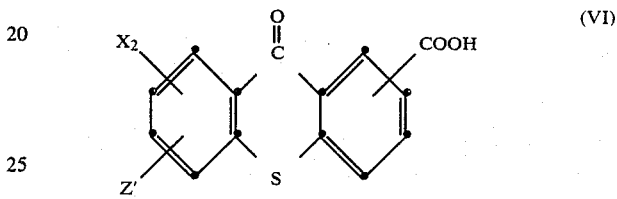

or (b) reacting a compound of the formula Vb

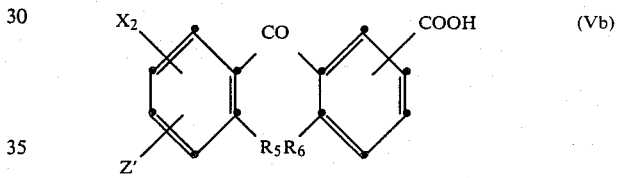

in which $R_5$ and $R_6$ independently of one another are a detachable group, with an inorganic sulfide to give a compound of the formula VI, reacting the compound of the formula VI, if desired after prior conversion to the acid chloride, with a compound of the formula HY to give a compound of the formula VII

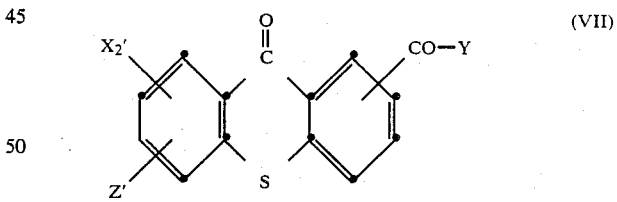

in which Y is as defined under formula I and Z' is as defined under formula Ia and $X_2'$ is hydrogen, halogen, —CN, —NO$_2$, —SO$_3$H, phenylsulfonyl or alkylsulfonyl, alkyl, alkoxy, alkylthio or dialkylamino, each having 1–4 C atoms in the alkyl moieties, —CO—OR$_1$, —CO—SR$_1$, —CO—N(R$_1$)(R$_2$), —CO—piperidyl, —CO—pyrrolidinyl or —CO—morpholinyl, and, if desired, subsequently converting the group $X_2'$ to a group X which differs from $X_2'$.

Only those compounds of the formula III in which $X_1$ and Z are not —OH or —SH are suitable for possible conversion to the acid chlorides (prior to the reaction with compounds of the formula HY). Chlorinating agents which can be used are, for example, thionyl chloride, PCl$_5$ or oxalyl chloride. Carboxyl groups $X_1$ or $X_2'$ are also chlorinated during this reaction. The acid chlorides ($X_1$ and $X_2$=—COCl and/or Y=chlorine) prepared from compounds of the formula III and VI are novel.

The intermediates of the formula VI or III can also be converted to compounds of the formula I by converting the said compounds to a corresponding alkali metal salt or alkaline earth metal salt, reacting the resulting salt with a compound of the formula Hal-Y, in which Y is as defined under formula I and Hal is a halogen atom, to give a compound of the formula I and, if desired, subsequently converting the groups $X_1$ or $X_2'$ to a group X which differs from $X_1$ or $X_2'$. An excess of the compound Hal-Y can also serve as the solvent.

The said reaction can also be carried out by means of phase transfer catalysis, for example in the presence of tetraalkylammonium halides or trialkylbenzylammonium halides, such as tetramethylammonium chloride, tetraethylammonium chloride, trimethylbenzylammonium chloride or triethylbenzylammonium chloride.

Finally, compounds of the formula Ib

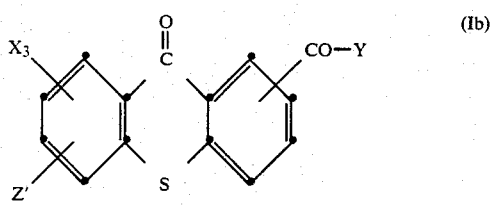

(Ib)

in which $X_3$ is a group corresponding to X but is not —CN, and Y and Z' are as defined under formula I or Ia, can also be prepared by reacting a compound of the formula IX

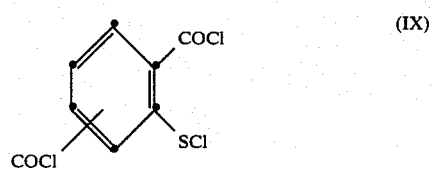

(IX)

in the presence of a Friedel-Crafts catalyst with a compound of the formula

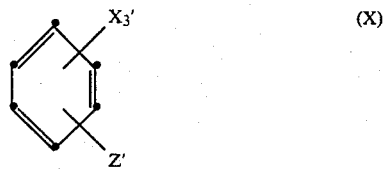

(X)

decomposing the resulting complex to give a compound of the formula XI

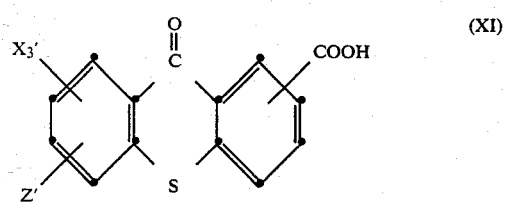

(XI)

in which $X_3'$ is hydrogen, halogen, —NO$_2$, —COOH, —SO$_3$H, phenylsulfonyl or alkylsulfonyl, alkyl, alkoxy, alkylthio, N,N-dialkylamino or —CO—alkyl, each having 1-4 C atoms in the alkyl moieties, —CO—OR$_1$ or —CO—SR$_1$, reacting the compound of the formula XI, if desired after prior conversion to the acid chloride, with a compound of the formula HY to give a compound of the formula XII

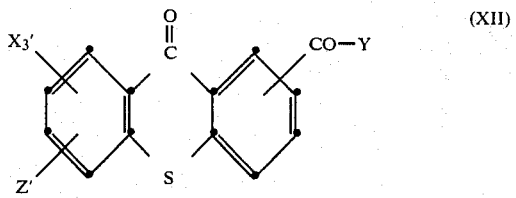

(XII)

in which $X_3'$, Z' and Y are as defined above, and, if desired, converting the group $X_3'$ to a group $X_3$ which differs from $X_3'$.

The cyclisation of the compounds of the formula IIa and IIb to give compounds of the formula III is advantageously carried out in the presence of a proton acid or of a Lewis acid. Examples of suitable proton acids are polyphosphoric acid, which can be mixed with phosphorus oxychloride, and chlorosulfonic acid and sulfuric acid. Examples of suitable Lewis acids are aluminium trichloride or boron trifluoride. Cyclisation in the presence of a proton acid is preferred. The reaction is preferably carried out at temperatures between about 0° and 240° C. and in particular between about 150° and 210° C.

Suitable detachable groups $R_3$ to $R_6$ are in particular halogen atoms and nitro, arylsulfonyl and sulfinyl groups. Preferred detachable groups $R_3$ to $R_6$ are halogen atoms, especially chlorine, and nitro groups.

The inorganic sulfide used for the reaction with compounds of the formula Vb is advantageously an alkali metal sulfide or hydrosulfide or alkaline earth metal sulfide or hydrosulfide, preferably sodium sulfide. The reaction temperatures for the cyclisation of the compounds of the formula Va and the reaction of the compounds of the formula Vb with an inorganic sulfide are advantageously between about 20° and 350° C. The reaction is preferably carried out in an organic solvent, in particular in an aprotic solvent. Suitable solvents are, for example, dialkylsulfoxides, such as dimethylsulfoxide, N,N-dialkylamides of aliphatic monocarboxylic acids having 1-3 C atoms, such as N,N-dimethylformamide and N,N-dimethylacetamide, and also N-methylpyrrolidone, hexamethylphosphoric acid triamide and sulfolane. It is also possible to use mixtures with other solvents, such as alcohols, for example 2-methoxyethanol, diethylene glycol monomethyl ether or diethylene glycol monoethyl ether. The starting materials of the formula Va and Vb can be obtained in a manner known per se, by a Friedel-Craft reaction of correspondingly substituted acyl halides with a suitably substituted nucleophilic aromatic compound.

The condensation reaction of the compounds of the formula IX with the compounds of the formula X in the presence of Friedel-Crafts catalysts (Lewis acids) is advantageously carried out in an organic medium at temperatures between about 10° and 80° C. In general, the reagents are added to the organic medium at a somewhat lower temperature, for example at between about 10° and 40° C. and in particular at between about 15° and 25° C. After all of the reagents, including the catalyst, have been added, the temperature can be raised to about 80° C. Suitable solvents for carrying out the Friedel-Crafts reaction are, for example, chlorinated aliphatic or aromatic hydrocarbons, such as methylene chloride, 1,2-dichloroethane, 1,2,3-trichloropropane, 1,1,2,2-tetrachloroethane and halogenated benzenes, such as dichlorobenzene.

Suitable Friedel-Crafts catalysts are, for example, aluminium chloride, aluminium bromide, zinc chloride, tin tetrachloride, boron trifluoride, iron-III chloride, titanium tetrachloride, phosphorus trichloride, phosphorus oxychloride, antimony pentafluoride and antimony pentachloride. Aluminum chloride is preferably used.

After the reaction has ended, the resulting complex can be decomposed by pouring into a water/ice mixture or by adding dilute mineral acid, such as hydrochloric acid, or aqueous alkali metal hydroxide or alkaline earth metal hydroxide solutions, such as sodium hydroxide, potassium hydroxide, barium hydroxide and calcium hydroxide.

The reaction of the compounds of the formula III or VI with a compound of the formula HY, and also the reaction of the corresponding acid chlorides or of the compounds of the formula XI with compounds of the formula HY, can, depending on the nature of the reactants, be carried out with or without the addition of an inert organic solvent, such as dioxan, methylene chloride, chloroform, acetone, benzene or toluene, and if desired can be carried out in the presence of an organic base, for example triethylamine or pyridine. For the preparation of the esters and thioesters, the solvent used is advantageously an excess of the corresponding alcohol or thiol. The preparation of the amides is preferably carried out in the presence of an inert organic solvent and of an excess of the corresponding amine.

The reaction with alcohols is advantageously carried out under reflux. The reaction temperatures for the reaction with thiols are in general between about 25° and 80° C., whilst the reaction with the amines is preferably carried out at between about 0° and 40° C. The reaction of the free acids of the formula III or VI is advantageously carried out in the presence of a dehydrating agent, such as HCl gas or concentrated sulfuric acid, and if desired with removal of the water as an azeotrope.

Compounds of the formula I in which Y is —NHR$_1$, and R$_1$ is alkyl as defined, can also be prepared by reacting carboxylic acid esters of the formula I, preferably the methyl or ethyl esters, with amines R$_1$NH$_2$ in the presence of suitable solvents, such as dioxan, tetrahydrofuran, methanol, ethanol, benzene or toluene.

The conversion of groups X$_1$, X$_2'$ and X$_3'$ to groups X and X$_3$ can be carried out in a manner known per se. Thus, for example, nitro groups X$_1$, X$_2'$ or X$_3'$ can be reduced by methods known per se to amino groups, which, in turn, can be converted to halogen atoms, —OH, —SH, —CN or alkoxy, N-alkylamino or N,N-dialkylamino groups. Cyano groups X$_1$ or X$_2$ can be converted to —CO—alkyl groups.

During the reaction with the compounds of the formula HY, carboxyl groups X$_1$, X$_2'$ and X$_3'$ are converted to —CO—OR$_1$, —CO—SR$_1$, —CO—N(R$_1$)(R$_2$), —CO—piperidyl, —CO—pyrrolidinyl or —CO—morpholinyl groups X.

Thioxanthones of the formula I which are substituted by alkylsulfonyl or phenylsulfonyl groups can be prepared, for example, by reacting the corresponding nitro compounds with alkali metal alkylsulfinates or alkali metal phenylsulfinates.

The starting compounds of the formulae IX and X are known or can be prepared by methods known per se. Compounds of the formula IIa and IIb can, for example, be prepared by a process analogous to that described in German Offenlegungsschrift No. 2,344,799, by reacting suitably substituted thiophenols or derivatives thereof, such as alkali metal salts or alkaline earth metal salts, with nitro- or halogeno-benzenes.

The thiophenol and the nitro- or halogeno-benzene together must contain at least two —COR or —COR' groups, or two groups which can be converted to —COR or —COR' groups, such as nitrile groups, one of which must be in the ortho-position relative to the SH group or to the nitro group or to the halogen atom. If a halogeno-benzene is used for the reaction, the formation of the diphenyl thioether of the formula IIa or IIb is advantageously effected by heating the reactants in the presence of NaOH or KOH in a high-boiling polar solvent, such as N,N-dimethylformamide or N,N-dimethylacetamide. Suitable halogenobenzenes are, for example, 2-, 3- and 4-chlorobenzoic acid.

Suitable nitrobenzenes are those which also contain, in addition to the nitro group, one or more electron-attracting groups, such as carboxylic acid ester groups, carboxylic acid chloride groups, nitrile groups, anhydride groups or imide groups. Examples of such nitrobenzenes are: phthalic anhydride, phthalic acid dinitrile, N-phenyl- or N-ethyl-nitrophthalimide, isophthalic acid dinitrile, terephthalic acid dinitrile, isophthalic acid dichloride, terephthalic acid dichloride and dialkyl esters of isophthalic acid and terephthalic acid, having 1-8 C atoms in the alkyl moieties in each case.

In accordance with a preferred process, esters of the formula XIII

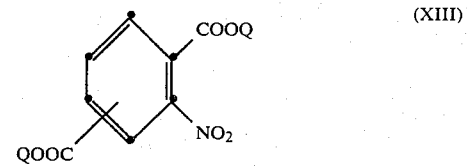

are reacted, in the presence of a base, with thiophenols of the formula XIV

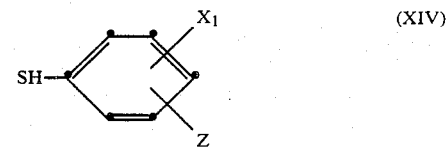

to give compounds of the formula XV

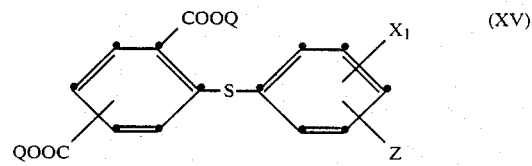

in which formula X$_1$ and Z are as defined above and the Qs independently of one another are alkyl having 1-8 C atoms or phenyl. Preferably, the two Qs have the same meaning and are alkyl having 1-6 C atoms. The above reaction is advantageously carried out in the presence of an inert organic solvent, such as N,N-dialkylamides of aliphatic monocarboxylic acids having 1-3 C atoms, for example N,N-dimethylformamide or N,N-dimethylacetamide, dimethylsulfoxide or hexamethylphosphoric acid amide. Suitable bases are, for example, alkali metal hydrides or hydroxides and alkaline earth metal hydrides or hydroxides, in particular sodium hydride, sodium hydroxide and potassium hydroxide. The compounds of the formula XV are subsequently saponified in a manner known per se to give compounds of the formula IIa.

The intermediates of the formula XV are novel with the exception of those in which $X_1$ and Z are each hydrogen and the two Qs are methyl and the —COOQ groups are in the m-position or p-position relative to one another. These novel compounds of the formula XV are likewise a subject of the invention.

As mentioned initially, the thioxanthone derivatives of the formula I, according to the invention, are used as photoinitiators. The invention therefore also relates to the use of compounds of the formula I as initiators for the photopolymerisation of ethylenically unsaturated compounds or for the photochemical crosslinking of polyolefines, and also to mixtures of (A) a compound of the formula I and (B) an organic amine, as initiators for the photopolymerisation of ethylenically unsaturated compounds or for the photochemical crosslinking of polyolefines.

The organic amines used can be aliphatic, aromatic, araliphatic, cycloaliphatic or heterocyclic amines. They can be primary, secondary or tertiary amines. Examples are butylamine, dibutylamine, tributylamine, cyclohexylamine, benzyldimethylamine, di-cyclohexylamine, triethylamine, phenyl-diethanolamine, piperidine, piperazine, morpholine, pyridine, quinoline, ethyl p-dimethylaminobenzoate or Michler's ketone (4,4'-bis-dimethylaminobenzophenone).

Preferred mixtures are those of (A) a compound of the formula I in which X and Z are each hydrogen and the group —CO—Y is in the 1-position or 3-position, in particular those in which Y is —O—alkyl, —NH—alkyl or —N(alkyl)(alkyl), each having 1-4 C atoms in the moieties, and (B) an aliphatic tertiary amine, an alkyl p-dimethylaminobenzoate or Michler's ketone.

Examples of aliphatic tertiary amines are trimethylamine, triethylamine, tri-isopropylamine, tributylamine, dodecyl-dimethylamine, octyl-dimethylamine, triethanolamine, tris-(hydroxypropyl)-amine, N-methyl-diethanolamine or N-butyl-diethanolamine.

Particularly preferred mixtures are those of (A) a compound of the formula I in which X and Z are each hydrogen and the group —CO—Y is in the 1-position or 3-position, in particular those in which Y is —O—alkyl, —NH—alkyl or —N(alkyl)(alkyl), each having 1-4 C atoms in the alkyl moieties, and (B) triethanolamine or a $C_1$-$C_4$—alkyldiethanolamine.

The mixtures according to the invention preferably contain the compounds of the formula I and the organic amines in a weight ratio of 4:1 to 1:4.

Examples of photopolymerisable compounds are unsaturated monomers, such as esters of acrylic or methacrylic acid, for example methyl acrylate, ethyl acrylate, n- or tert.-butyl acrylate, isooctyl acrylate or hydroxyethyl acrylate, methyl methacrylate or ethyl methacrylate, ethylene diacrylate, butanediol diacrylate, hexanediol diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide and N-substituted (meth)-acrylamide; vinyl esters, for example vinyl acetate, vinyl propionate, vinyl acrylate or vinyl succinate; other vinyl compounds, such as vinyl esters, vinyl ketones, vinyl sulfones, styrene, alkylstyrenes, halogenostyrenes, divinylbenzene, N,N'-divinylurea, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether, and the mixtures of such unsaturated monomers.

The mixtures according to the invention are particularly suitable for the photopolymerisation of acrylic acid esters and mixtures thereof.

Further examples are unsaturated acrylic resins. These include, for example, reaction products of polyepoxides (epoxy resins) with acrylic acid or methacrylic acid or reaction products of polyisocyanates with hydroxyalkyl acrylates and also the reaction products of hydroxyl group-containing polyesters or polyethers with acrylic acid or methyacrylic acid. In most cases, these unsaturated acrylic resins are used as a mixture with one or more acrylates of a mono-, di or polyalcohol, for example ethyl acrylate, butyl acrylate, benzyl acrylate, 2-ethylhexyl acrylate or 2-hydroxypropyl acrylate, ethylene glycol diacrylate, propylene glycol diacrylate, butanediol diacrylate, hexamethylene diacrylate, trimethylolpropane trisacrylate or pentaerythritol tetraacrylate.

The invention also relates to photopolymerisable systems consisting of (a) at least one ethylenically unsaturated compound, (b) a mixture of (A) and (B), as defined, and, if desired, (c) other additives, such as inhibitors, stabilisers, UV absorbers, fillers, pigments, dyes, agents for imparting thixotropic properties and levelling assistants, for example silicone oil.

Inhibitors which are employed and which are intended to provide protection against premature polymerisation, in particular during the preparation of the systems by mixing the components, are, for example, hydroquinone, hydroquinone derivatives, p-methoxyphenyl or β-naphthols. Examples of UV absorbers which can be employed are those of the benztriazole or benzophenone type.

Suitable fillers are, for example, silicic acid, talc or gypsum.

Preferred photopolymerisable systems are those in ratios of 99.5–80% by weight of (a) and (c) to 0.5–20% by weight of (b).

Preferably, an acrylic acid ester or a mixture of several acrylic acid esters is used as component (a).

In particular, the photopolymerisable systems according to the invention are a printing ink or a white lacquer.

Combinations with known photoinitiators which form free radicals as a result of photofragmentation, for example benzoin ethers, dialkoxyacetophenones or benzil ketals, can also be used.

The initiator mixtures according to the invention are very important for the photocuring of printing inks and coatings containing white pigments, since the drying time of the binder is a decisive factor in determining the production speed of graphical products and should be of the order of magnitude of fractions of a second. The initiators according to the invention are also very suitable for photocurable systems for the production of printing plates.

A further field of application is the UV curing of coatings on metal, for example in the lacquer coating of sheet metal for tubes, cans or bottle closures, and also the UV curing of plastic coatings, for example floor or wall coverings based on PVC.

Examples of the UV curing of coatings on paper are the colourless lacquer-coating of labels, gramophone record sleeves or book jackets.

The mixtures according to the invention can also be used as initiators for photochemical crosslinking of polyolefines. Suitable polyolefines are, for example, polypropylene, polybutene and polyisobutylene and also copolymers, for example ethylene/propylene copolymers, but preferably polyethylene of low, moderate or high density.

The addition of the photoinitiators to the photopolymerisable systems is in general effected by simply stirring in, since most of these systems are liquid or readily soluble. Usually, the initiators dissolve, which ensures their uniform distribution and also transparency of the polymers.

Polymerisation is effected by the known methods for photopolymerisation, by irradiation with light rich in short-wave radiation. Suitable light sources are, for example, medium-pressure, high-pressure and low-pressure mercury vapour lamps and also superactinic fluorescent tubes, the emission maxima of which are in the range between 250 and 450 nm.

For the photochemical crosslinking of polyolefines, the photoinitiator is added to the polyolefine before or during shaping, for example by mixing in powder form or by mixing with the plasticised polyolefine. Crosslinking is effected by irradiation of the shaped article in solid form, for example in the form of films or fibres.

The compounds of the formula I, according to the invention, are also suitable as sensitisers for photocrosslinkable polymers of very diverse types. Such polymers are used, for example, for the production of printing plates for the offset printing process, for the preparation of photo offset lacquers and for unconventional photography, for example for the production of photographic images by means of photopolymerisation or photocrosslinking. Such polymers are used in particular as so-called photoresists for the production of printed circuits by methods known per se. For this purpose, that side of the printed circuit board which is provided with the light-sensitive coating is exposed through a transparent negative carrying the image of the printed circuit and then developed, after which the unexposed areas of the coating are removed by developer liquid.

Polymers which can be used are, per se, any desired materials for which the sensitivity to light (sensitivity towards actinic radiation) can be increased by the use of the compounds of the formula I, according to the invention. The compounds of the formula I are very particularly suitable for sensitisers for polymers of the type described in German Offenlegungsschrift No. 2,626,769, i.e. polymers which contain, as light-sensitive groups, groups of the formula XVI

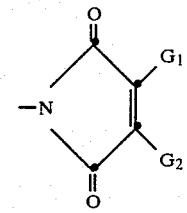

in which $G_1$ and $G_2$ independently of one another are alkyl having 1–4 C atoms, especially methyl, or $G_1$ and $G_2$ together make up the members required to complete a 5-membered to 6-membered carbocyclic ring.

The compounds of the formula I can be incorporated in the photocrosslinkable polymers in a manner known per se. The content of compounds of the formula I in the polymer can vary greatly depending on the intended use and the number of photocrosslinkable groups present in the polymer, but in general is between about 0.1 and 20%, based on the weight of the polymer.

PREPARATION EXAMPLES (a) Preparation of the starting materials

Example A: Thioxanthone-1-carboxylic acid

Dry sodium thiophenolate prepared from 7.5 g (0.33 gram equivalent) of sodium, 300 ml of methanol and 36 ml (0.33 mol) of thiophenol is dissolved in 300 ml of dimethylsulfoxide, and 80.4 g (0.3 mol) of 3-nitrophthalic acid N-phenylimide are added. The reaction mixture is heated at 50° C. for 90 minutes and then poured into a mixture of 300 ml of water and 300 ml of anhydrous acetic acid. The resulting suspension is filtered with suction and the product is dried at 80° C./13,000 Pa. 100 g (100% of theory) of 3-phenylthiophthalic acid N-phenylimide are obtained.

99.4 g (0.3 mol) of 3-phenylthiophthalic acid N-phenylimide are suspended in 1,326 ml of a 20% sodium hydroxide solution and the suspension is heated at 100° C. for 30 minutes, with stirring. After cooling, the alkaline suspension is acidified with 672 ml of 37% hydrochloric acid, with stirring. After one hour, the fine suspension is filtered with suction and the material on the suction filter is suspended, while still wet, in 882 ml of 37% hydrochloric acid and the resulting suspension is refluxed for one hour. The reaction mixture is cooled, the resulting fine suspension is filtered with suction and the product is dried at 80° C./13,000 Pa. 69.4 g (85% of theory) of 3-phenylthiophthalic acid are obtained.

69 g (0.25 mol) of 3-phenylthiophthalic acid and 700 ml of polyphosphoric acid are heated at 200° C. for 90 minutes, with stirring, and the mixture is then cooled and stirred into 3,000 ml of water. After one hour, the resulting suspension is filtered with suction and the material on the filter is washed with water and dried at 80° C. The resulting crude product is dissolved hot in 350 ml of N,N-dimethylformamide, animal charcoal is added and the mixture is filtered. The filtrate is diluted with five times the amount of water, the resulting suspension is filtered and the material on the filter is washed with water and dried. This yields 63 g (98% of theory) of thioxanthone-1-carboxylic acid; melting point 259° C. The acid obtained in this way can be further used direct.

Example B: Thioxanthone-1-carboxylic acid chloride 82 g (0.32 mol) of thioxanthone-1-carboxylic acid are boiled in 460 ml of thionyl chloride for 5 hours under reflux. The resulting dark, clear solution is evaporated to dryness. 87.5 g (100% of theory) of thioxanthone-1-carboxylic acid chloride are obtained.

Example C: Thioxanthone-3-carboxylic acid (a) 10.0 g (0.23 mol) of a sodium hydride dispersion (55% by weight in paraffin) are added in portions to 24.24 g (0.22 mol) of thiophenol in 150 ml of N,N-dimethylformamide. After the exothermic reaction has subsided (30 minutes), 47.84 g (0.20 mol) of methyl nitroterephthalate are added and the mixture is heated at 65°–70° C. for 1.5 hours. After cooling to room temperature (20°–25° C.), 300 ml of water are poured in and the product (diester) which has precipitated is filtered off. This diester is refluxed in a solution of 28.0 g (0.5 mol) of potassium hydroxide in 500 ml of methanol for 1.5 hours, the reaction mixture is concentrated and 250 ml of water are added. The heterogeneous reaction mixture is washed with methylene chloride (3× with 150 ml in each case), the aqueous phase is treated with active charcoal and filtered and the filtrate is concentrated. The filtrate is then acidified with concentrated sulfuric acid and the precipitate which has separated out is filtered off. After drying in vacuo at 80° C., 37.9 g (69% of theory) of 2-phenylthio-terephthalic acid remain; melting point >250° C.

Elementary analysis for $C_{14}H_{10}O_4S$ (molecular weight 274.3): calculated C 61.31% H 3.68% found C 61.05% H 3.56%.

IR spectrum (KBr): 1690 $cm^{-1}$.

(b) 25 g (0.091 mol) of 2-phenylthio-terephthalic acid are added in portions to 200 ml of ice-cooled chlorosulfonic acid at a rate such that the temperature of the reaction mixture remains between 5° and 10° C. The mixture is stirred for a further 1 hour at 5°–10° C. and is poured carefully onto ice. The thioxanthone-3-carboxylic acid which has precipitated is filtered off and dried in vacuo at 100° C. 23.9 g (100% of theory) of yellow crystalline thixanthone-3-carboxylic acid are obtained; melting point >250° C. For analysis, 1 g is recrystallised hot from 200 ml of anhydrous acetic acid.

Elementary analysis for $C_{14}H_8O_3S$ (molecular weight 256.27): calculated C 65.62% H 3.15% found C 65.01% H 3.07%.

IR spectrum (KBr): 1630 $cm^{-1}$.

UV spectrum (N,N-dimethylformamide): $\lambda_{max.}=390$ nm, $\epsilon=5732$.

Example D: Thioxanthone-7-methyl-3-carboxylic acid (a) 2-(4-Methylphenylthio)-terephthalic acid, prepared analogously to Example C; melting point >250° C. (75% of theory); IR spectrum (KBr): 1690 $cm^{-1}$.

Elementary analysis for $C_{15}H_{12}O_4S$ (molecular weight 288.32): calculated C 62.49% H 4.20% found C 62.56% H 4.28%.

2-(4-Methylphenylthio)-terephthalic acid can also be prepared as follows: 90.2 g (0.726 mol) of p-thiocresol are dissolved in 600 ml of N,N-dimethylformamide, after which 31.7 g (0.792 mol) of finely powdered sodium hydroxide are added. After stirring for half an hour at 20°–25° C., 158.0 g (0.660 mol) of dimethyl nitroterephthalate are added to the homogeneous solution and the reaction mixture is stirred for 1.5 hours at 70° C. After cooling to 20°–25° C., 1000 ml of water are added and the precipitate which has separated out is filtered off. 275 g of moist product are obtained. This is refluxed in a solution of 89.5 g of KOH in 1200 ml of methanol for one hour. The reaction mixture is cooled to 20°–25° C., 1000 ml of water and a little active charcoal are added and the resulting mixture is filtered after stirring for half an hour. The filtrate is freed from methanol in a rotary evaporator and the residual aqueous phase is extracted with three times 200 ml of methylene chloride. The precipitate formed on acidifying the aqueous phase with sulfuric acid is filtered off and washed with water. After drying in vacuo at 80° C., 140 g (74% of theory) of 2-(4-methylphenylthio)-terephthalic acid remain.

(b) Cyclisation to thioxanthone-7-methyl-3-carboxylic acid analogously to Example C (99% of theory); IR spectrum (KBr): 1640 $cm^{-1}$; UV spectrum (N,N-dimethylformamide): $\lambda_{max.}=395$ nm, $\epsilon=5733$.

Example E: Thioxanthone-7-chloro-3-carboxylic acid (a) 2-(4-Chlorophenylthio)-terephthalic acid, prepared analogously to Example C: melting point >250° C. (66% of theory); IR spectrum (KBr): 1690 $cm^{-1}$.

Elementary analysis for $C_{14}H_9ClO_4S$ (molecular weight 308.74): calculated C 54.47% H 2.94% found C 54.24% H 3.18%.

(b) Cyclisation of thioxanthone-7-chloro-3-carboxylic acid analogously to Example C (90% of theory); UV spectrum (N,N-dimethylformamide): $\lambda_{max.}=400$ nm, $\epsilon=14,242$.

Example F: Thioxanthone-7-methoxy-3-carboxylic acid (a) 2-(4-Methoxyphenylthio)-terephthalic acid, prepared analogously to Example C, paragraph (a); melting point >250° C. (65% of theory); IR spectrum (KBr): 1690 $cm^{-1}$.

Elementary analysis for $C_{15}H_{12}O_5S$ (molecular weight 304.32): calculated C 59.21% H 3.98% found C 58.49% H 3.88%.

(b) 35.2 g (0.116 mol) of 2-(4-methoxyphenyl)-terephthalic acid are refluxed with 350 ml of phosphorus oxychloride for 2 hours (bath temperature 120° C.). The dark, heterogeneous reaction mixture is evaporated in a rotary evaporator, and 500 ml of water are added to the residue, with ice-cooling. The resulting mixture is stirred for 1 hour at room temperature and filtered and the product is dried in vacuo at 70° C. 32.6 g (98% of theory) of solid, orange-colored thioxanthone-7-methoxy-3-carboxylic acid remain. IR spectrum (KBr): 1640 $cm^{-1}$; UV spectrum (N,N-dimethylformamide): $\lambda_{max.}=410$ nm, $\epsilon=5633$.

Example G: Thioxanthone-7-methyl-2-carboxylic acid (a) 2-(4-Methylphenylthio)-isophthalic acid, prepared analogously to Example C, paragraph (a); melting point >250° C.; (68% of theory); IR spectrum (KBr): 1690 $cm^{-1}$.

Elementary analysis for $C_{15}H_{12}O_4S$ (molecular weight 288.32): calculated C 62.49% H 4.20% found C 62.40% H 4.20%.

(b) Cyclisation to thioxanthone-7-methyl-2-carboxylic acid analogously to Example F, paragraph (b), (98% of theory); melting point 205°–208° C. IR spectrum (KBr): 1645 $cm^{-1}$.

Example H: Thioxanthone-7-methoxy-1-carboxylic acid

Prepared analogously to Example A using p-methoxythiophenol in place of thiophenol.

Elementary analysis for $C_{15}H_{10}O_4S$ (molecular weight 286.30): calculated C 62.93% H 3.52% S 11.20% found C 61.7% H 3.2% S 11.3%.

IR spectrum (KBr): 1640 cm$^{-1}$ (—CO—)

Example I: Thioxanthone-7-methoxy-1-carboxylic acid chloride

Obtained from the above compound by reacting with thionyl chloride analogously to Example B.

(b) Preparation of compounds of the formula I

Example 1

20.5 g (0.0747 mol) of thioxanthone-1-carboxylic acid chloride, 5 ml of methanol and 300 ml of dioxan are refluxed for 2 hours, the reaction mixture is then evaporated to dryness and the residue is stirred with a saturated solution of sodium bicarbonate. The resulting suspension is filtered with suction and the product is washed with water, dried and recrystallised from 300 ml of methanol with the addition of animal charcoal. This yields 11.3 g (83.7% of theory) of methyl thioxanthone-1-carboxylate; melting point 138°–140° C.

IR spectrum (chloroform): 1750 cm$^{-1}$ (—COOR), 1660 cm$^{-1}$ (—CO—)

Elementary analysis for $C_{15}H_{10}O_3S$ (molecular weight 270.3): calculated C 66.6% H 3.7% S 11.8% found C 66.7% H 3.7% S 11.6%.

Example 2

13.7 g (0.05 mol) of thioxanthone-1-carboxylic acid chloride, 7.4 g (0.1 mol) isobutyl alcohol and 200 ml of dioxan are refluxed for 2 hours. After working up as described in Example 1 and after recrystallisation from 300 ml of methanol with the addition of animal charcoal, 11.5 g (76.6% of theory) of isobutyl thioxanthone-1-carboxylate are obtained; melting point 141°–142° C.

IR spectrum (dioxan) 1750 cm$^{-1}$ (—COOR), 1660 cm$^{-1}$ (—CO—).

Elementary analysis for $C_{18}H_{16}O_3S$ (molecular weight 312.38): calculated C 69.2% H 5.2% S 10.3% found C 69% H 4.9% S 10.4%.

Example 3

9.1 g (0.033 mol) of thioxanthone-1-carboxylic acid chloride, 8.11 g (0.033 mol) of 1-octadecanol and 130 ml of dioxan are refluxed for 2 hours. The reaction mixture is worked up as described in Example 1. After recrystallising from 1000 ml of methanol with the addition of animal charcoal, 1-octadecyl thioxanthone-1-carboxylate is obtained and this is purified by dissolving in 1000 ml of chloroform and stirring with 158 g of $SiO_2$. After filtering of the $SiO_2$ with suction and evaporating the chloroform solution, 8 g (52.4% of theory) of 1-octadecyl thioxanthone-1-carboxylate are obtained; melting point 76°–77° C.

IR spectrum (dioxan): 1750 cm$^{-1}$ (—COOR), 1660 cm$^{-1}$ (—CO—).

Elementary analysis for $C_{32}H_{44}O_3S$ (molecular weight 508.76): calculated C 75.5% H 8.7% S 6.3% found C 75.5% H 8.8% S 6.1%.

Example 4

12.1 g (0.044 mol) of thioxanthone-1-carboxylic acid chloride, 7.45 g (0.04 mol) of 1-dodecanol and 170 ml of dioxan are refluxed for 2 hours. The reaction mixture is worked up as described in Example 1. After treating the reaction product with 25 g of $SiO_2$ in 200 ml of chloroform, 12.1 g (71% of theory) of 1-dodecyl thioxanthone-1-carboxylate are obtained; melting point 61° C.

IR spectrum (dioxan): 1750 cm$^{-1}$ (—COOR), 1660 cm$^{-1}$ (—CO—).

Example 5

15.1 g (0.055 mol) of thioxanthone-1-carboxylic acid chloride, 6.51 g (0.05 mol) of 1-octanol and 210 ml of dioxan are refluxed for 2 hours. The reaction mixture is then worked up as described in Example 1. After-treatment of the reaction product with 150 g of $SiO_2$ in 200 ml of chloroform yields 13.2 g (71.7% of theory) of 1-octyl thioxanthone-1-carboxylate; melting point 54°–55° C.

IR spectrum (dioxan): 1750 cm$^{-1}$ (—COOR), 1660 cm$^{-1}$ (—CO—).

Elementary analysis for $C_{26}H_{32}O_3S$ (molecular weight 424.6): calculated C 73.5% H 7.6% S 7.5% found C 73.0% H 7.5% S 7.3%.

Example 6

15.1 g (0.055 mol) of thioxanthone-1-carboxylic acid chloride, 11 g (0.11 mol) of cyclohexanol and 210 ml of dioxan are refluxed for 2 hours. The reaction mixture is worked up as described in Example 1. After recrystallising the crude product from 300 ml of methanol, 14.51 g (78% of theory) of cyclohexyl thioxanthone-1-carboxylate are obtained; melting point 176° C. IR spectrum (dioxan): 1750 cm$^{-1}$ (—COOR), 1660 cm$^{-1}$ (—CO—).

Elementary analysis for $C_{20}H_{18}O_3S$ (molecular weight 338.4): calculated C 70.9% H 5.3% S 9.4% found C 70.4% H 5.3% S 9.2%.

Example 7

2 g (0.0073 mol) of thioxanthone-1-carboxylic acid chloride, 1.2 g (0.0077 mol) of 2-decanol and 50 ml of dioxan are refluxed for 2 hours and the reaction mixture is then evaporated to dryness. The reaction product is dissolved in 100 ml of chloroform and the resulting solution is three times extracted by shaking with, in each case, 100 ml of saturated sodium bicarbonate solution. The chloroform solution is evaporated to dryness. 2 g (72% of theory) of 2-decyl thioxanthone-1-carboxylate are obtained (in the form of an oil).

IR spectrum (dioxan): 1750 cm$^{-1}$ (—COOR), 1660 cm$^{-1}$ (—CO—).

Elementary analysis for $C_{24}H_{28}O_3S$ (molecular weight 396.5): calculated C 72.7% H 7.1% S 8.1% found C 72.9% H 7.2% S 7.9%.

Example 8

27.4 g (0.1 mol) of thioxanthone-1-carboxylic acid chloride, 18 g (0.11 mol) of triethylene glycol monomethyl ether and 250 ml of dioxan are refluxed for 2 hours, after which the reaction mixture is evaporated to dryness. The residue is taken up in 800 ml of methylene chloride and this solution is extracted with saturated sodium chloride solution. The organic phase is separated off, dried over sodium sulfate and treated with 100 g of $SiO_2$. After filtering off the sodium sulfate and the $SiO_2$, with suction, the solution is evaporated, the residue is dissolved in 100 ml of methanol and the solution is filtered with animal charcoal. The solution is then evaporated. This yields 21.5 g (53.2% of theory) of the triethylene glycol monomethyl ether-ester of thioxanthone-1-carboxylic acid (in the form of an oil).

IR spectrum (chloroform) 1750 cm$^{-1}$ (—COOR), 1660 cm$^{-1}$ (—CO—).

Elementary analysis for $C_{21}H_{22}O_6S$ (molecular weight 402.46): calculated C 62.7% H 5.5% O 2.38% S 8.0% found C 62.7% H 5.4% O 2.38% S 8.0%.

Example 9

1.46 g (0.02 mol) of n-butylamine are added dropwise at not more than 35° C. to a solution of 2.74 g (0.01 mol) of thioxanthone-1-carboxylic acid chloride in 80 ml of dioxan. After leaving to stand at 25° C. for 12 hours, the reaction mixture is evaporated to dryness, the residue is stirred with water and the resulting suspension is extracted with chloroform. The chloroform extract is dried over sodium sulfate, stirred with 0.5 g of aluminium oxide and filtered. The chloroform solution is then evaporated to dryness. This yields 0.8 g (26% of theory) of thioxanthone-1-carboxylic acid N-n-butyl-amide; melting point 164° C.

IR spectrum (chloroform) 1670 cm$^{-1}$ (—CONH—), 1660 cm$^{-1}$ (—CO—).

Elementary analysis for $C_{18}H_{17}NO_2S$ (molecular weight 311.4): calculated C 69.4% H 5.5% N 4.5% S 10.3% found C 69.2% H 5.6% N 4.5% S 10.2%.

Example 10

5 g (0.0195 mol) of thioxanthone-3-carboxylic acid are refluxed with 30 ml of thionyl chloride for 2 hours. The dark, homogeneous reaction solution is evaporated in a rotary evaporator. 100 ml of methanol are added to the residue, with ice-cooling. The resulting mixture is refluxed for 3 hours and cooled in ice and the precipitate which has separated out is filtered off. after drying in vacuo at 60° C., 4.5 g (90% of theory) of yellow, crystalline methyl thioxanthone-3-carboxylate are obtained; melting point 164°-165° C.

IR spectrum (KBr): 1640 cm$^{-1}$. UV spectrum (N,N-dimethylformamide): $\lambda_{max.}=395$ nm, $\epsilon=5807$.

Elementary analysis for $C_{15}H_{10}O_3S$ (molecular weight 270.31): calculated C 66.60% H 3.72% found C 66.10% H 3.61%.

Examples 11-19

The following compounds are prepared in a manner analogous to that described in Example 5, using the corresponding starting thioxanthones and alcohols:

Ethyl thioxanthone-3-carboxylate; melting point 146°-147° C. (93.7% of theory); IR spectrum (KBr): 1645 cm$^{-1}$; UV spectrum (N,N-dimethylformamide): $\lambda_{max.}=395$ nm, $\epsilon=5744$.

Elementary analysis for $C_{16}H_{12}O_3S$ (molecular weight 284.34): calculated C 67.59% H 4.26% found C 67.43% H 4.23% (compound No. 11).

n-Butyl thioxanthone-3-carboxylate; melting point 125°-127° C. (70% of theory); IR spectrum (KBr): 1645 cm$^{-1}$; UV spectrum (N,N-dimethylformamide): $\lambda_{max.}=395$ nm, $\epsilon=5712$.

Elementary analysis for $C_{18}H_{16}O_3S$ (molecular weight 312,4): calculated C 69.21% H 5.17% found C 69.25% H 5.13% (compound No. 12).

β-Methoxyethyl thioxanthone-3-carboxylate; melting point 126°-130° C.; IR spectrum (KBr): 1640 cm$^{-1}$, UV spectrum (N,N-dimethylformamide: $\lambda_{max.}=395$ nm, $\epsilon=5416$.

Elementary analysis for $C_{17}H_{14}O_4S$ (molecular weight 314.36): calculated C 64.96% H 4.49% found C 64.75% H 4.49% (compound No. 13)

Ethyl thioxanthone-7-chloro-3-carboxylate; melting point 175°-178° C.; yield 77% of theory; IR spectrum (KBr): 1645 cm$^{-1}$; UV spectrum (N,N-dimethylformamide): $\lambda_{max.}=400$ nm, $\epsilon=5767$.

Elementary analysis for $C_{16}H_{11}ClO_3S$ (molecular weight 318.78): calculated C 60.29% H 3.48%. found C 60.24% H 3.51% (compound No. 14).

n-Butyl thioxanthone-7-chloro-3-carboxylate; melting point 137°-140° C. Yield 93% of theory.

IR Spectrum (KBr): 1645 cm$^{-1}$; UV spectrum (N,N-dimethyl-formamide): $\lambda_{max.}=400$ nm, $\epsilon=5877$.

Elementary analysis for $C_{18}H_{15}ClO_3S$ (molecular weight 346.83): calculated C 62.34% H 4.36% found C 62.33% H 4.41% (compound No. 15).

β-Methoxyethyl thioxanthone-7-chloro-3-carboxylate. Melting point 155°-158° C.; yield 98% of theory.

IR spectrum (KBr): 1645 cm$^{-1}$; UV spectrum (N,N-dimethylformamide): $\lambda_{max.}=400$ nm, $\epsilon=5743$.

Elementary analysis for $C_{17}H_{13}ClO_4S$ (molecular weight 348.81): calculated C 58.54% H 3.76% found C 58.56% H 3.74% (compound No. 16).

Methyl thioxanthone-7-methyl-2-carboxylate; melting point 165°-168° C.; yield 89% of theory.

IR spectrum (KBr): 1645 cm$^{-1}$; UV spectrum (N,N-dimethylformamide): $\lambda_{max.}=385$ nm, $\epsilon=5340$.

Elementary analysis for $C_{16}H_{12}O_3S$ (molecular weight 284.33): calculated C 67.59% H 4.26% found C 67.30 H 4.16% (compound No. 17).

Ethyl thioxanthone-7-methyl-2-carboxylate; melting point 128°-130° C.; yield 84% of theory.

IR spectrum (KBr): 1645 cm$^{-1}$; UV spectrum (N,N-dimethylformamide): $\lambda_{max.}=385$ nm, $\epsilon=5316$.

Elementary analysis for $C_{17}H_{14}O_3S$ (molecular weight 298.36): calculated C 68.44% H 4.73% found C 68.42% H 4.64% (compound No. 18).

β-Methoxyethyl thioxanthone-7-methyl-2-carboxylate; melting point 121°-124° C.; yield 77% of theory.

IR spectrum (KBr): 1645 cm$^{-1}$; UV spectrum (N,N-dimethylformamide): $\lambda_{max.}=385$ nm, $\epsilon=5437$.

Elementary analysis for $C_{18}H_{16}O_4S$ (molecular weight 328.39): calculated C 65.84% H 4.92% found C 65.66% H 4.83% (compound No. 19)

Examples 20-23

5 g (0.0185 mol) of thioxanthone-7-methyl-3-carboxylic acid are kept under reflux with 30 ml of thionyl chloride and a few drops of N,N-dimethylformamide for 2 hours. The dark reaction solution is evaporated in a rotary evaporator, and 100 ml of methanol are added to the residue with ice-cooling. The resulting mixture is refluxed for 3 hours and cooled in ice, and the precipitate which has separated out is filtered off. After drying in vacuo at 60° C., this yields 4.8 g (91% of theory) of methyl thioxanthone-7-methyl-3-carboxylate; melting point 171°-174° C.

IR spectrum (KBr): 1640 cm$^{-1}$; UV spectrum (N,N-dimethylformamide: $\lambda_{max.}=410$ nm, $\epsilon=5422$.

Elementary analysis for $C_{16}H_{12}O_3S$ (molecular weight 284.34): calculated C 67.59% H 4.26% found C 67.41% H 4.14% (compound No. 20).

The following compounds are prepared in a manner analogous to that described above:

Ethyl thioxanthone-7-methyl-3-carboxylate; melting point 153°–155° C. (95% of theory); IR spectrum (KBr): 1640 cm$^{-1}$; UV spectrum (N,N-dimethylformamide): $\lambda_{max.}=405$ nm, $\epsilon=5691$.

Elementary analysis for $C_{17}H_{14}O_3S$ (molecular weight 298.36): calculated C 68.44% H 4.73% found C 68.56% H 4.72% (compound No. 21).

n-Butyl thioxanthone-7-methyl-3-carboxylate; melting point 117°–118° C. (92% of theory); IR spectrum (KBr): 1640 cm$^{-1}$; UV spectrum (N,N-dimethylformamide): $\lambda_{max.}=402$ nm, $\epsilon=5629$.

Elementary analysis for $C_{19}H_{18}O_3S$ (molecular weight 326.42): calculated C 69.92% H 5.56% found C 69.95% H 5.52% (compound No. 22).

β-Methoxyethyl thioxanthone-7-methyl-3-carboxylate; melting point 116°–118° C. (60% of theory); IR spectrum (KBr): 1645 cm$^{-1}$; UV spectrum (N,N-dimethylformamide): $\lambda_{max.}=403$ nm, $\epsilon=5336$.

Elementary analysis for $C_{18}H_{16}O_4S$ (molecular weight 326.37): calculated C 65.84% H 4.92% found C 65.79% H 4.91% (compound No. 23).

Examples 24–26

5 g (0.0175 mol) of thioxanthone-7-methoxy-3-carboxylic acid and 100 ml of thionyl chloride are refluxed for 2 hours. Excess thionyl chloride is removed in a rotary evaporator, and 100 ml of methanol are added to the residue, after which the reaction mixture is refluxed for 3 hours. The reaction mixture is cooled in ice and the precipitate is filtered off and dried in vacuo at 80° C. 4.9 g of yellow, crystalline methyl thioxanthone-7-methoxy-3-carboxylate remain; melting point 192°–195° C. (93% of theory). IR spectrum (KBr): 1640 cm$^{-1}$; UV spectrum (N,N-dimethylformamide): $\lambda_{max.}=415$ nm, $\epsilon=5673$.

Elementary analysis for $C_{16}H_{12}O_4S$ (molecular weight 300.23): calculated C 63.99% H 4.03% found C 63.29% H 3.88% (compound No. 24).

The following compounds are prepared in a manner analogous to that described above:

Ethyl thioxanthone-7-methoxy-3-carboxylate; melting point 176°–178° C.; yield 93% of theory.

IR spectrum (KBr): 1640 cm$^{-1}$; UV spectrum (N,N-dimethylformamide): $\lambda_{max.}=415$ nm, $\epsilon=5561$.

Elementary analysis for $C_{17}H_{14}O_4S$ (molecular weight 314.36): calculated C 64.96% H 4.49% found C 64.80% H 4.35% (compound No. 25).

β-Methoxyethyl thioxanthone-7-methoxy-3-carboxylate; melting point 105°–107° C.; yield 52% of theory.

IR Spectrum (KBr): 1640 cm$^{-1}$; UV spectrum (N,N-dimethylformamide): $\lambda_{max.}=415$ nm, $\epsilon=5650$.

Elementary analysis for $C_{18}H_{16}O_5S$ (molecular weight 344.39): calculated C 62.78% H 4.69% found C 62.67% H 4.57% (compound No. 26).

Example 27

12.9 g (0.1 mol) of di-n-butylamine are added dropwise, at a temperature not above 35° C., to a solution of 13.7 g (0.05 mol) of thioxanthone-1-carboxylic acid chloride in 400 ml of dioxan. After leaving to stand for 51 hours at 25° C., the di-n-butylamine hydrochloride which has precipitated is filtered off and the dark-coloured filtrate is evaporated to dryness. The residue is dissolved in 100 ml of methanol and, after adding animal charcoal, the solution is filtered and the filtrate is evaporated to dryness. The residue is dissolved in 200 ml of chloroform and the solution is stirred vigorously with 50 g of neutral aluminium oxide for 30 minutes and filtered. After evaporating the chloroform, this yields 9.7 g (54.5% of theory) of thioxanthone-1-carboxylic acid N,N-di-n-butylamide; melting point 79°–81° C. IR spectrum (chloroform) 1670 cm$^{-1}$ (—CO—NH—), 1640 cm$^{-1}$ (—CO—).

Elementary analysis for $C_{22}H_{25}NO_2S$ (molecular weight 367.48): calculated C 71.93% H 6.81% N 3.81% S 8.72% found C 71.95% H 6.71% N 3.84% S 8.61%.

Example 28

5 g (0.016 mol) of thioxanthone-7-methoxy-1-carboxylic acid chloride, 5 ml of ethanol and 50 ml of dioxan are refluxed for 2 hours. The reaction mixture is worked up as described in Example 1. After recrystallising from 300 ml of ethanol, ethyl thioxanthone-7-methoxy-1-carboxylate is obtained in a yield of 3.4 g (65% of theory); melting point: 185° C.

Elementary analysis for $C_{17}H_{14}O_4S$ (molecular weight 314.36): calculated C 64.95% H 4.48% S 10.19% found C 63.8% H 4.2% S 10.3%

IR spectrum (chloroform): 1735 cm$^{-1}$ (—COOR) 1650 cm$^{-1}$ (—CO—)

UV spectrum (chloroform): $\lambda_{max.}$: 405 nm $\epsilon_{max}$: 6000

Use examples

Example I: Curing of a blue printing ink

A blue printing ink is prepared in accordance with the following recipe: 55.0 parts by weight of Setalin AP 560 (acrylic resin from Synthese, Holland), 20.0 parts by weight of Irgalith GLSM (blue pigment from Ciba-Geigy), 4.0 parts by weight of a photoinitiator of the formula I, 4.0 parts by weight of N-methyldiethanolamine and 17.0 parts by weight of Ebecryl 150 (acrylic resin from UCB-Belgium).

A blue coloured paste is prepared from the Setalin AP 560 and the Irgalith GLSM on a three-roll mill.

The photocuring agent is predissolved with the amine in Ebecryl 150 and the resulting solution is incorporated in the blue coloured paste by dispersing on a muller machine. The printing ink is then applied in a coating of 1.5 g/m$^2$ to special paper with the aid of a Prüfbau proof press.

| Printing conditions: | |
| --- | --- |
| Printing pressure: | 25 Kp/cm$^2$ |
| Printing speed | 2 m/second. |

Immediately after making the proof, the sampler are cured in one pass by irradiating in a UV apparatus (manufacturer: Radiation Polymer Company USA) at a variable transport speed.

| Equipment conditions: | |
| --- | --- |
| Power of the lamp | 80 W/cm (standard mercury vapour lamp) |
| Lamp distance | 11 cm. |

The set-off test is used to assess the curing. In the test the speed is determined at which no further transfer of printing ink to neutral paper can be determined under a printing pressure of 25 Kp/cm$^2$. The abrasion test using a REL SCRATCH HARDNESS RECORDER according to Defense Specification DEI-1053 Method No. 8, is also carried out. The measured values obtained with the thioxanthone derivatives according to the invention are listed in the following table. The numbers in the second column give the printing speed in m/second which is possible if no transfer of the printing ink is to result in the set-off test. The higher this speed, the more rapid is the curing of the printing ink. The figures in the third column indicate the speed at which the abrasion test is passed.

| Initiator used | Set-off test | REL test |
|---|---|---|
| 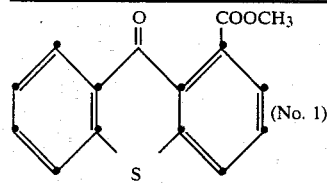 (No. 1) | 2.0 | 2.0 |
| 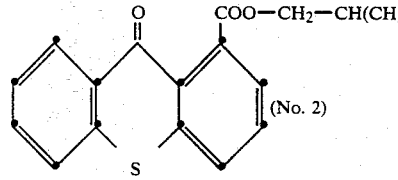 (No. 2) | 1.75 | 1.5 |

Example II: Curing of a blue printing ink

A blue printing ink is prepared in accordance with the following recipe:

(A) Stock paste: 165 g of Setalin AP 560 (acrylic resin from Synthese, Holland), 45 g of carbon black (carbon black 2/C from Degussa, Federal Republic of Germany), 15 g of Vossenblau 362 (pigment from CIBA-GEIGY) and 27 g of Ebecryl 150 (acrylic resin from UCB, Belgium).

The coloured paste is prepared on a three-roll mill.

(B) Photoinitiator solution: 1 g of a photoinitiator of the formula I, 1 g of N-methyldiethanolamine and 2 g of Ebecryl 150.

0.8 g of the photoinitiator solution (B) is incorporated in 4.2 g of the stock paste (A) by dispersion on a muller machine. The printing ink is then applied in a coating of 2.0 g/m² to special paper with the aid of a Prüfbau proof press and cured as described in Example I. As in Example I, curing is evaluated by means of the set-off test and the abrasion test. The measured values obtained for this printing ink recipe are listed in the following table.

| Photoinitiator used | Set-off test | REL test |
|---|---|---|
| 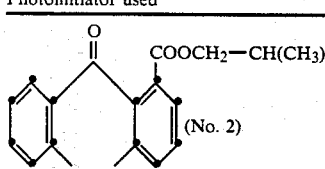 (No. 2) | 0.28 | 0.55 |
| 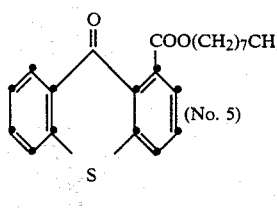 (No. 5) | 0.55 | 1.10 |
| 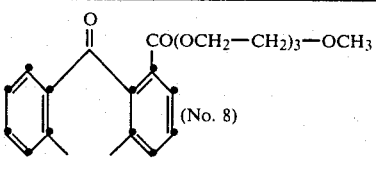 (No. 8) | 0.28 | 1.65 |
| 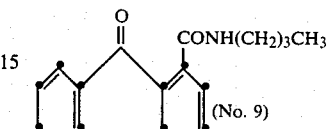 (No. 9) | 1.10 | 0.82 |
| 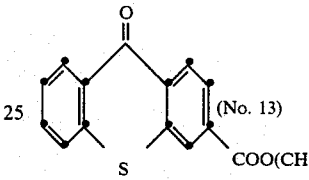 (No. 13) | 0.28 | 0.55 |
| 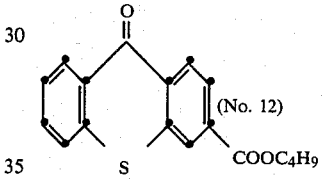 (No. 12) | 0.28 | 0.82 |
| 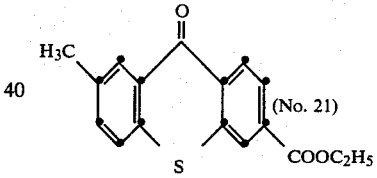 (No. 21) | 0.28 | 0.82 |
| 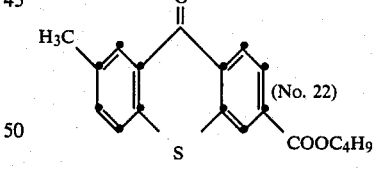 (No. 22) | 0.82 | 0.82 |
| 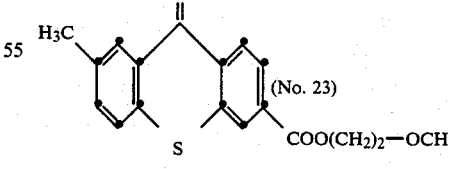 (No. 23) | 1.10 | 1.36 |
| 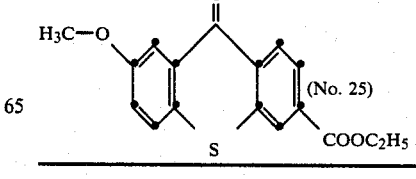 (No. 25) | 0.55 | 0.55 |

Example III: Curing of a white lacquer

A white lacquer is prepared in accordance with the following recipe: 1.94 g of PLEX 6631 (acrylic resin from Röhm & Haas, Federal Republic of Germany), 0.53 g of 2-hydroxypropyl acrylate, 2.47 g of titanium dioxide RTC-2 (titanium dioxide for Thioxide, England), 0.13 g of N-methyldiethanolamine, 0.26 g of a photoinitiator of the formula I and 1.02 g of hexanediol diacrylate.

The mixture, without hexanediol diacrylate, is twice ground for 200 revolutions with the aid of a muller machine under a weight of 7.5 kg. The hexanediol diacrylate is then added to the ground mixture.

The white lacquer prepared in this way is applied to glass plates using a 40 μm doctor. The samples are irradiated using a UV exposure apparatus (standard Hg vapour lamp; power of the lamp 80 W/cm; lamp distance 11 cm, conveyor belt speed=50 m/minute). The following four tests are used to assess the curing of the white lacquer samples:

1. Wipe resistance: The number of passes of the sample through the irradiation apparatus required to obtain a wipe-resistant surface is determined.
2. Pendulum hardness: The samples are passed through the UV irradiation apparatus 10 times. The König pendulum hardness is then determined (DIN 53,157).
3. Gloss: The samples are passed through the UV irradiation apparatus 10 times. The gloss is measured with the aid of a multigloss apparatus (DIN 67,530) at an angle of 60°.
4. Yellowness index: The samples are passed through the UV irradiation apparatus 10 times. The yellowness index is determined with the aid of a colour measuring instrument.

The values obtained are given in the table which follows:

| Photoinitiator of the formula I | Wipe resistance | Pendulum hardness | Gloss | Yellowness index |
|---|---|---|---|---|
| 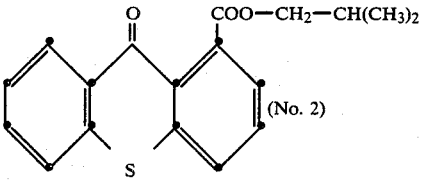 (No. 2) | 2 | 153" | 88 | 2 |
| 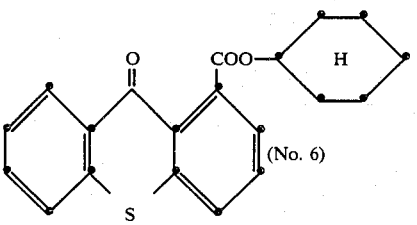 (No. 6) | 3 | 127" | 88 | 0 |
| 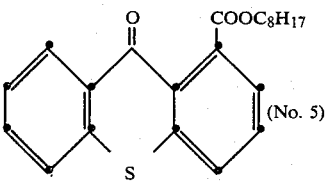 (No. 5) | 2 | 175" | 90 | 2 |
| 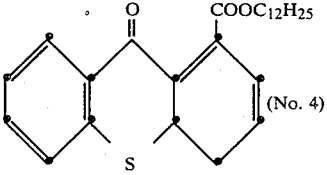 (No. 4) | 2 | 148" | 91 | 3 |
| 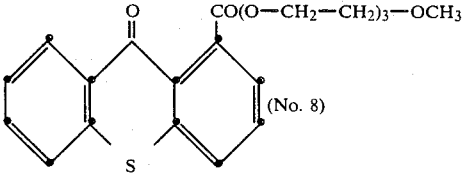 (No. 8) | 2 | 169" | 89 | 1 |

| Photoinitiator of the formula I | Wipe resistance | Pendulum hardness | Gloss | Yellowness index |
|---|---|---|---|---|
| (No. 3) benzophenone with COOC₁₈H₃₇ and S substituents | 8 | 137" | 57 | 0 |
| (No. 9) benzophenone with CONHC₄H₉ and S substituents | 3 | 169" | 94 | 0 |
| (No. 12) benzophenone with COOC₄H₉ and S substituents | 4 | 136" | 86 | 1 |
| (No. 13) benzophenone with COO—CH₂—CH₂—OCH₃ and S substituents | 4 | 130" | 87 | 5 |
| (No. 21) methyl-benzophenone with COOC₂H₅ and S substituents | 2 | 138" | 85 | 7 |

Example IV: Production of images by photocrosslinking (a) Preparation of the polymers

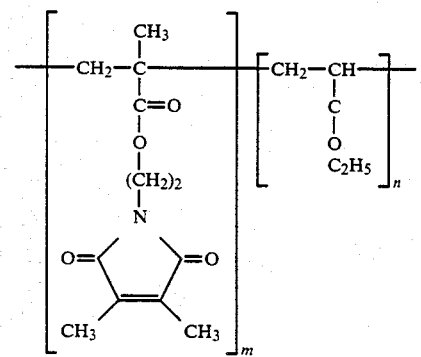

465.5 g (1.963 mols) of N-(β-methacroyloxyethyl)-dimethylmaleimide ester [prepared according to German Offenlegungsschrift No. 2,626,769] are dissolved together with 49.15 g (0.49 mol) of ethyl acrylate in 960 ml of 1-acetoxy-2-ethoxy-ethane, under nitrogen. A solution of 3.86 g of azoisobutyronitril in 25 ml of 1-acetoxy-2-ethoxyethane is allowed to run in at 80° C., under a nitrogen atmosphere, and the mixture is then polymerised for 6 hours. The solution is stabilised, while still hot, with 2.57 g of 2,6-di-tert.-butyl-p-cresol. Viscosity of the solution, measured with a Höppler falling ball viscometer in accordance with DIN 53,015 = 829 × 10⁻³ Pa s (polymer I); average molecular weight (measured by light scattering in chloroform) = 1,000,000.

When the above example is repeated using only 3.1 g of azoisobutyronitrile, but an otherwise identical procedure, a polymer (polymer II) is obtained wihich has an average molecular weight (measured by light scattering in chloroform) of No. 1,235,838. Viscosity of the solution, measured with a Höppler falling ball viscometer in accordance with DIN 53,015 = 1253 × 10⁻³ Pa s, intrinsic viscosity = 0.51 dl/g in chloroform.

(b) Production of images

The amounts of sensitiser indicated in Tables I, II and III, which follow, are added to 100 g amounts of the polymer solutions described under (a). Copper-laminated epoxide sheets are coated by whirl-coating (500 revolutions/minute for 1 minute) with the polymer solutions, which have been diluted to a 15% by weight solids content, in such a way that, after drying, a 1–3μ thick polymer coating is formed on the copper. The coated sheets are exposed through a negative original (step wedge Stauffer 21-step sensitivity guide) as follows: using either a 400 Watt high-pressure mercury vapour lamp at a distance of 55 cm from the vacuum table or a 1000 Watt metal halide lamp at a distance of 60 cm from the vacuum table.

After exposure, the image is developed for 2 minutes in a 1,1,1-trichloroethanol bath, by which means the parts which have not been crosslinked are dissolved out. The resulting relief image of the depicted step wedge is rendered more easily visible by etching the copper portions with a 50% $FeCl_3$ solution.

In Tables I–III, which follow, $S_{rel}$ signifies the relative sensitivity. This factor indicates how much longer (or shorter) than 3 minutes the exposure time has to be for an image of step 7 (optical density=1) of the step wedge still to be formed.

This factor is determined as described in "Photoresist", W. S. De Forest, Mc Graw-Hill Book Company (N.Y.) 1975, pages 184 et seq.

TABLE I

Polymer II, exposed using a 400 Watt high-pressure mercury vapour lamp

| Polymer composition | | Sensitiser | Sensitizer concentration | | Photosensitivity last step depicted after | | | | |
|---|---|---|---|---|---|---|---|---|---|
| $\frac{m}{m+n}$ | $\frac{n}{m+n}$ | | % by weight* | Mol | 30" | 1' | 3' | 6' | $S_{rel}$ |
| 0.8 | 0.2 | 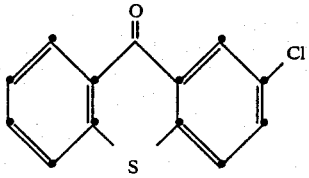 (according to the prior art) | 2.7<br>1.38<br>0.46 | $10.9 \cdot 10^{-3}$<br>$5.59 \cdot 10^{-3}$<br>$1.86 \cdot 10^{-3}$ | 4<br>2<br>0 | 6<br>4<br>1 | 9<br>8<br>5 | 11<br>10<br>7 | 2.00<br>1.41<br>0.50 |
| 0.8 | 0.2 | 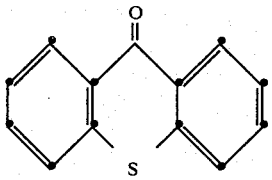 (according to the prior art) | 2.7<br>1.38<br>0.46 | $12.72 \cdot 10^{-3}$<br>$6.50 \cdot 10^{-3}$<br>$2.17 \cdot 10^{-3}$ | 4<br>2<br>0 | 6<br>4<br>2 | 9<br>7<br>5 | 11<br>9<br>7 | 2.00<br>1.00<br>0.50 |
| 0.8 | 0.2 | 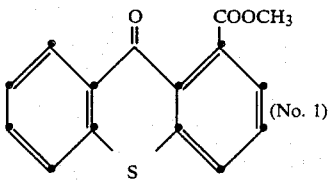 (No. 1) | 2.7<br>1.38<br>0.46 | $9.99 \cdot 10^{-3}$<br>$5.11 \cdot 10^{-3}$<br>$1.70 \cdot 10^{-3}$ | 5<br>3<br>0 | 7<br>5<br>2 | 10<br>10<br>6 | 11<br>11<br>7 | 2.83<br>2.83<br>0.71 |
| 0.8 | 0.2 | 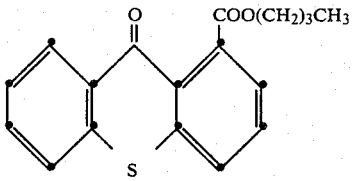 | 2.7<br>1.38<br>0.46 | $8.64 \cdot 10^{-3}$<br>$4.42 \cdot 10^{-3}$<br>$1.47 \cdot 10^{-3}$ | 4<br>3<br>0 | 7<br>5<br>2 | 9<br>8<br>5 | 11<br>10<br>7 | 2.00<br>1.41<br>0.50 |
| 0.8 | 0.2 | 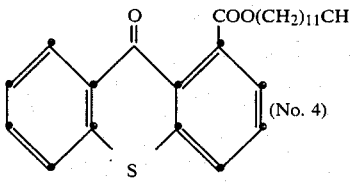 (No. 4) | 2.7<br>1.38<br>0.46 | $6.36 \cdot 10^{-3}$<br>$3.25 \cdot 10^{-3}$<br>$1.08 \cdot 10^{-3}$ | 3<br>1<br>0 | 5<br>4<br>1 | 8<br>6<br>4 | 10<br>9<br>6 | 1.41<br>0.71<br>0.35 |
| 0.8 | 0.2 | 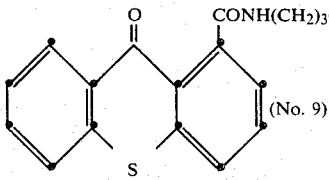 (No. 9) | 2.7<br>1.38<br>0.46 | $8.67 \cdot 10^{-3}$<br>$4.43 \cdot 10^{-3}$<br>$1.48 \cdot 10^{-3}$ | | | 11<br>8<br>6 | | 4.00<br>1.41<br>0.71 |

TABLE I-continued

Polymer II, exposed using a 400 Watt high-pressure mercury vapour lamp

| Polymer composition | | | Sensitizer concentration | | Photosensitivity last step depicted after | | | | |
|---|---|---|---|---|---|---|---|---|---|
| $\frac{m}{m+n}$ | $\frac{n}{m+n}$ | Sensitiser | % by weight* | Mol | 30″ | 1′ | 3′ | 6′ | $S_{rel}$ |
| 0.8 | 0.2 | [structure with CON(CH₂)₃CH₃ groups] (No. 27) | 2.7 | $7.35 \cdot 10^{-3}$ | 1 | 4 | 7 | 8 | 1.00 |
|  |  |  | 1.38 | $3.75 \cdot 10^{-3}$ | 0 | 2 | 5 | 7 | 0.50 |
|  |  |  | 0.46 | $1.25 \cdot 10^{-3}$ | 0 | 0 | 2 | 5 | 0.18 |

*% by weight, based on the weight of the polymer.

TABLE II

Polymer I, exposed using a 400 Watt high-pressure mercury vapour lamp

| Polymer composition | | | Sensitiser concentration | | Photosensitivity last step depicted after | | | | |
|---|---|---|---|---|---|---|---|---|---|
| $\frac{m}{m+n}$ | $\frac{n}{m+n}$ | Sensitiser | % by weight* | Mol | 30″ | 1′ | 3′ | 6′ | $S_{rel}$ |
| 0.8 | 0.2 | [structure CH₃...COOC₂H₅] (No. 18) | 2.7 | $9.05 \cdot 10^{-3}$ | 1 | 4 | 7 | 9 | 1.00 |
|  |  |  | 1.38 | $4.63 \cdot 10^{-3}$ | 0 | 2 | 5 | 8 | 0.50 |
|  |  |  | 0.46 | $1.54 \cdot 10^{-3}$ | 0 | 2 | 5 | 7 | 0.50 |
| 0.8 | 0.2 | [structure CH₃...COOC₂H₅] (No. 21) | 2.7 | $9.05 \cdot 10^{-3}$ | 6 | 8 | 11 | 12 | 4.00 |
|  |  |  | 1.38 | $4.63 \cdot 10^{-3}$ | 4 | 7 | 10 | 11 | 2.83 |
|  |  |  | 0.46 | $1.54 \cdot 10^{-3}$ | 2 | 4 | 7 | 9 | 1.00 |

*% by weight, based on the weight of the polymer.

TABLE III

Polymer II, exposed using a 1000 Watt metal halide lamp

| Polymer composition | | | Sensitiser concentration | | Photosensitivity last step depicted after 30″ |
|---|---|---|---|---|---|
| $\frac{m}{m+n+o}$ | $\frac{n}{m+n+o}$ | Sensitiser | % by weight* | mol | |
| 0.8 | 0.2 | [thioxanthone structure] (according to the prior art) | 2 | $9.42 \cdot 10^{-3}$ | 6 |
| 0.8 | 0.2 | [structure with COOCH₃] (No. 1) | 2 | $7.40 \cdot 10^{-3}$ | 7 |

TABLE III-continued

Polymer II, exposed using a 1000 Watt metal halide lamp

| Polymer composition | | | Sensitiser concentration | | Photosensitivity last step depicted |
|---|---|---|---|---|---|
| $\dfrac{m}{m+n+o}$ | $\dfrac{n}{m+n+o}$ | Sensitiser | % by weight* | mol | after 30" |
| 0.8 | 0.2 | 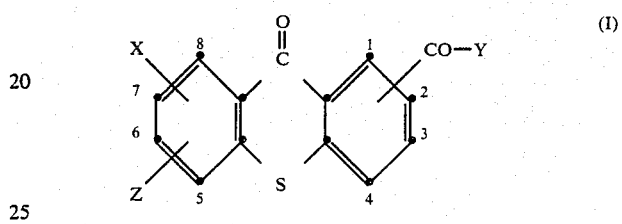 (No. 21) | 2 | $6.70 \cdot 10^{-3}$ | 9 |

*% by weight, based on the weight of the polymer.

It can be seen from the above Tables I to III that, compared with unsubstituted thioxanthone, which is a known compound, the thioxanthones according to the invention are distinguished by a markedly increased photosensitivity, in that approximately the same or even a greater number of steps can be rendered visible with substantially smaller amounts of sensitiser (amounts which are up to 50% smaller). In general, the thioxanthones according to the invention also have a higher relative sensitivity.

What is claimed is:

1. A compound of the formula I $$\text{(I)}$$

in which X is hydrogen, Z is bonded in the 7-position and is hydrogen, or alkyl having 1–4 C atoms, Y is —OR$_1$, R$_1$ is alkyl having 1–18 atoms, cyclohexyl or —(CH$_2$CH$_2$O)$_n$—CH$_3$, and n is an integer from 2 to 10, the group —CO—Y being bonded in the 1-position or 3-position.

2. A compound according to claim 1, of the formula I, in which Z is hydrogen.

3. A compound according to claim 1, in which Y is —OR$_1$ and R$_1$ is alkyl having 1–18 C atoms, or cyclohexyl.

4. A compound according to claim 1, in which Z is methyl.

5. A compound according to claim 1, of the formula I, in which X is hydrogen, Z is hydrogen or alkyl, the group —CO—Y is bonded in the 1-position or 3-position and Y is alkoxy having 1–18 C atoms.

* * * * *